US00PP20373P2

(12) United States Plant Patent
Álamo et al.

(10) Patent No.: US PP20,373 P2
(45) Date of Patent: Sep. 29, 2009

(54) BLUEBERRY PLANT NAMED 'ROMERO'

(50) Latin Name: *Vaccinium corymbosum*
Varietal Denomination: Romero

(75) Inventors: Antonio Abad Álamo, Huelva (ES); José Ulf Hayler López, Huelva (ES); Paul M. Lyrene, Gainesville, FL (US)

(73) Assignee: Royal Berries S.L., Almonte, Huelva (ES)

( * ) Notice: Subject to any disclaimer, the term of this patent is extended or adjusted under 35 U.S.C. 154(b) by 0 days.

(21) Appl. No.: 12/213,079

(22) Filed: Jun. 13, 2008

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers very early and forms fruit that ripens very early. The attractive dark blue berries exhibit a pleasant acid flavor and commonly are amenable to harvest without stem retention. The plant is self-fertile, is an excellent pollen producer, and displays a strong and vigorous generally upright growth habit with attractive evergreen foliage. A low chilling requirement is also exhibited.

5 Drawing Sheets

Botanical/commercial classification: *Vaccinium corymbosum* L./Blueberry Plant.

Varietal denomination: cv. Romero.

SUMMARY OF THE INVENTION

The new Blueberry cultivar of the present invention was the product of controlled artificial pollination carried out in a greenhouse at Greenwood, Fla., U.S.A., wherein two parents were crossed which previously had been studied in the hope that they would contribute the desired characteristics. The female parent (i.e., the seed parent) was the unreleased 'FL 95-3' cultivar (non-patented in the United States). The male parent (i.e., pollen parent) was the 'Star' cultivar (U.S. Plant Pat. No. 10,675). The parentage of the new cultivar can be summarized as follows:

'FL 95-3'×'Star'.

The seeds resulting from the pollination were shipped to Almonte, Huelva, Spain, where they sown during approximately 1997, small plants were obtained which were physically and biologically different from each other and selective research of the progeny was carried out. Selective study resulted in the identification of a single plant of the new cultivar. The new plant initially was designated SO1-18-12 .

It was found that the new Blueberry plant of the present invention displays the following combination of characteristics:

(a) flowers very early and forms fruit that ripens very early,
(b) displays a strong and vigorous generally upright growth habit with attractive evergreen foliage,
(c) is self-fertile and is an excellent pollen producer,
(d) displays a low chilling requirement, and
(e) forms in abundance attractive dark blue berries that exhibit a pleasant acid flavor which commonly are amenable to harvest without stem retention.

The new cultivar well meets the needs of the horticultural industry and can be grown to advantage for the commercial production of blueberries.

The new cultivar of the present invention can be distinguished from its ancestors and all other Blueberry cultivars known to its originators. When compared to the 'Sharpblue' cultivar (non-patented in the United States), the new cultivar is taller and more upright. When compared to the 'Gulf Coast' cultivar (non-patented in the United States), the berries of the new cultivar commonly can be harvested without the retention of stems unlike the 'Gulf Coast' cultivar. When compared to the 'Misty' cultivar (non-patented in the United States), the new cultivar forms dark blue berries while the fruit of the 'Misty' cultivar commonly is lighter blue in coloration. When compared to the 'O'Neal' cultivar (non-patented in the United States), the new cultivar commonly displays a chill requirement on the order of 200 hours, while the chill requirement of the 'O'Neal' cultivar commonly approximates 500 hours. When compared to the 'Star' cultivar (U.S. Plant Pat. No.10, 675), the new cultivar commonly ripens approximately four weeks earlier at Almonte, Huelva, Spain.

The new cultivar has been asexually reproduced by the rooting of cuttings beginning during the spring of 2001 at Almonte, Huelva, Spain. Such asexual propagation has shown that the characteristics of the new cultivar are firmly fixed and are stably transmitted from one generation to another. Accordingly, the new cultivar asexually reproduces in a true to type manner.

The new cultivar has been named 'Romero'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants which had been asexually reproduced by the rooting of cuttings were approximately five years of age except where otherwise indicated, and were being grown outdoors at Almonte, Huelva, Spain. All photographs were obtained during March-April, 2008 except where otherwise indicated.

FIG. 1 shows Feb. 8, 2007 an overall view of a typical fruiting plant of the new cultivar where primarily immature berries are apparent.

FIG. 2 was obtained on Feb. 8, 2007 and shows the flowers of the new cultivar as well as the foliage.

DETAILED DESCRIPTION

Figure 1:
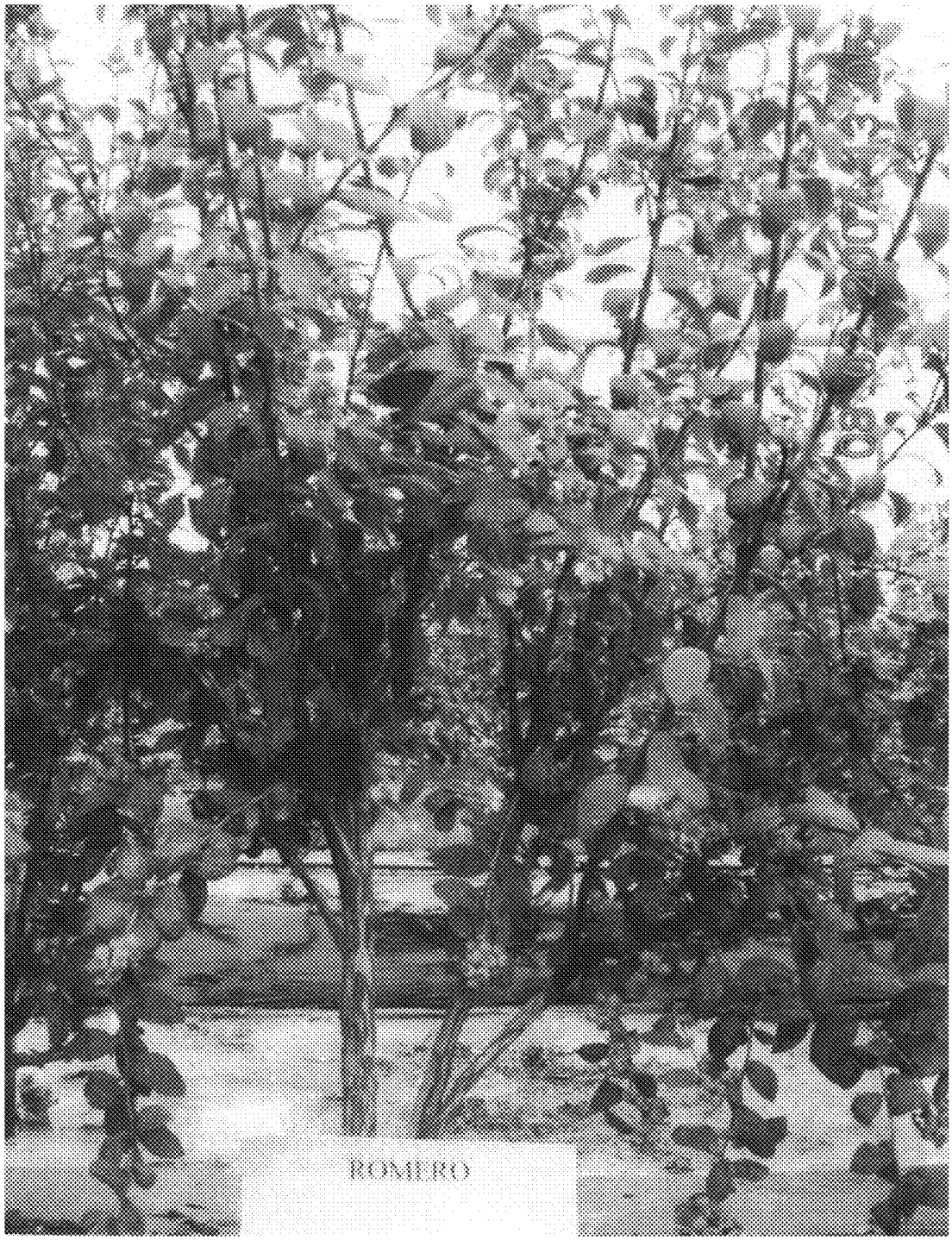
Figure 2:
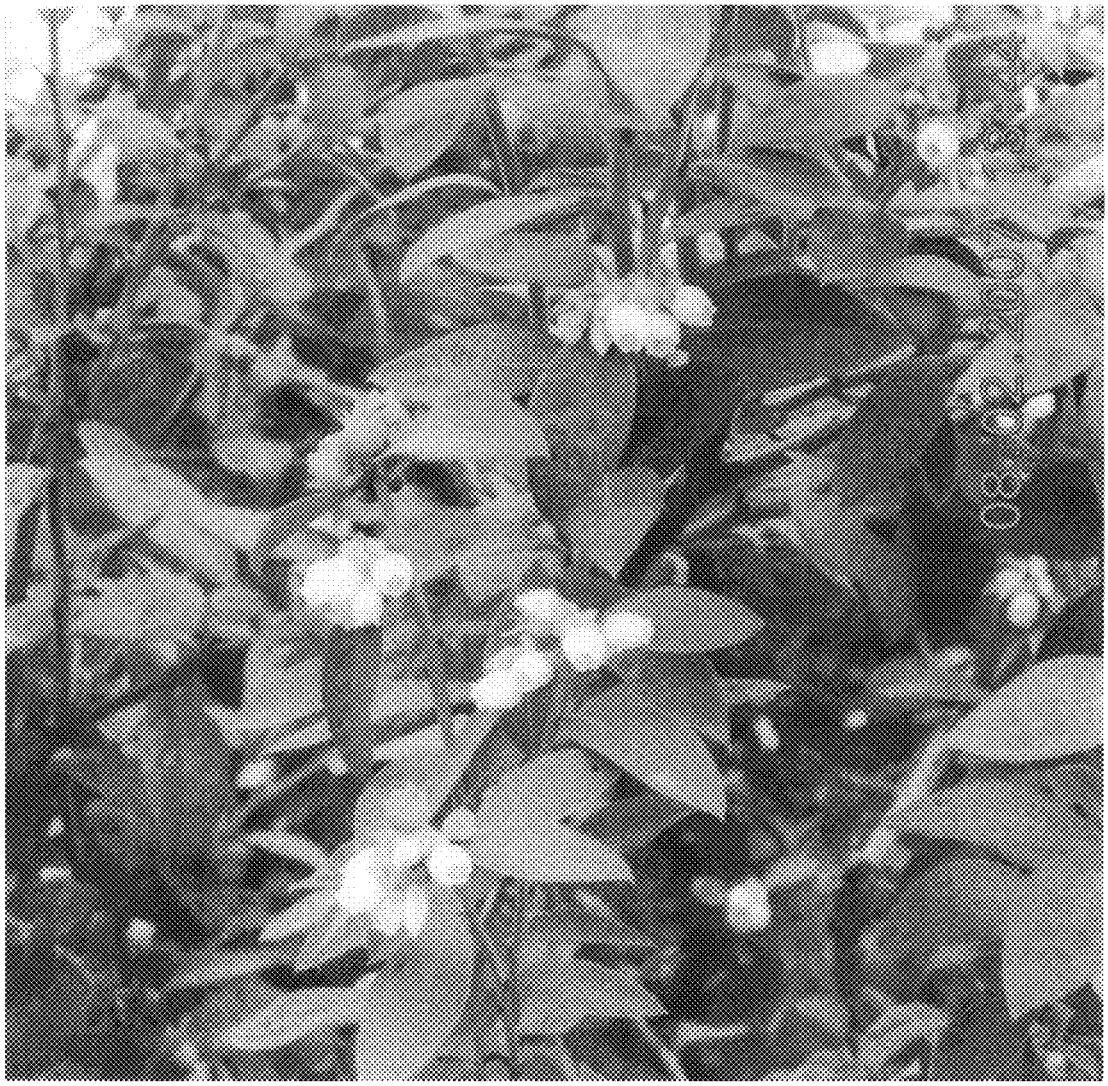
Figure 3:
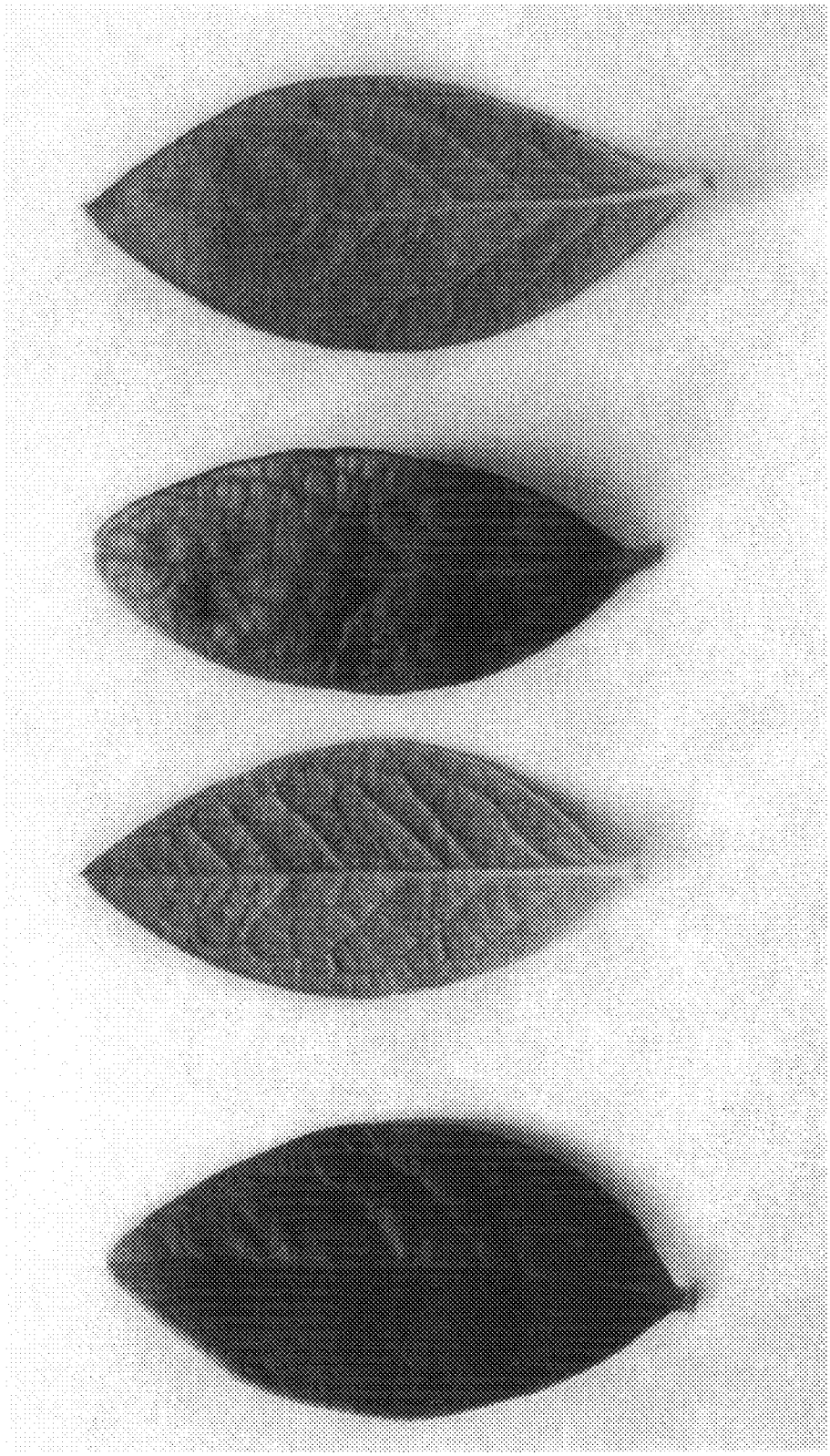
FIG. 3 shows a close view of typical leaves (both surfaces) of the new cultivar.
Figure 4:
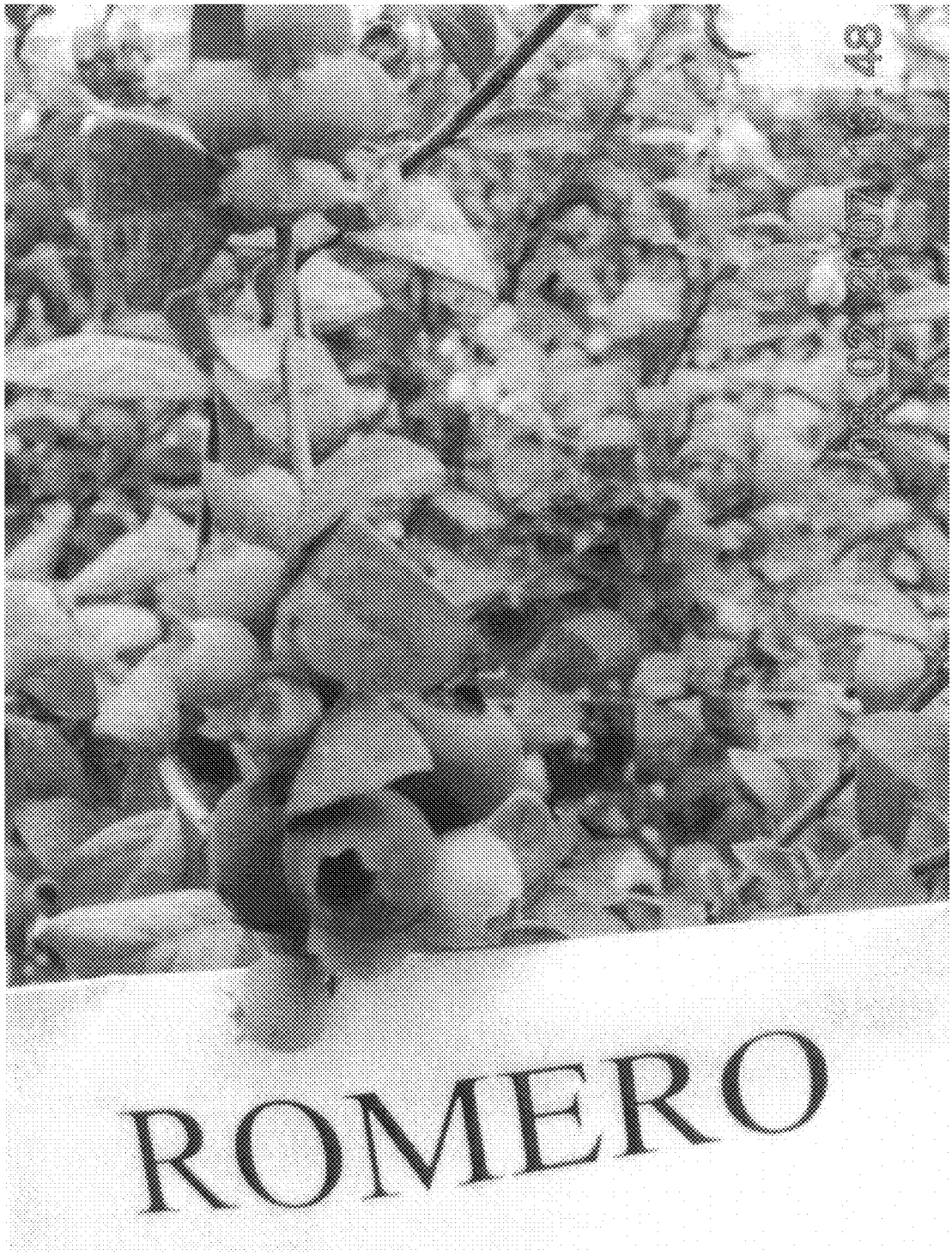
FIG. 4 shows typical berries of the new cultivar in various stages of maturity as well as the foliage of the new cultivar.
Figure 5:
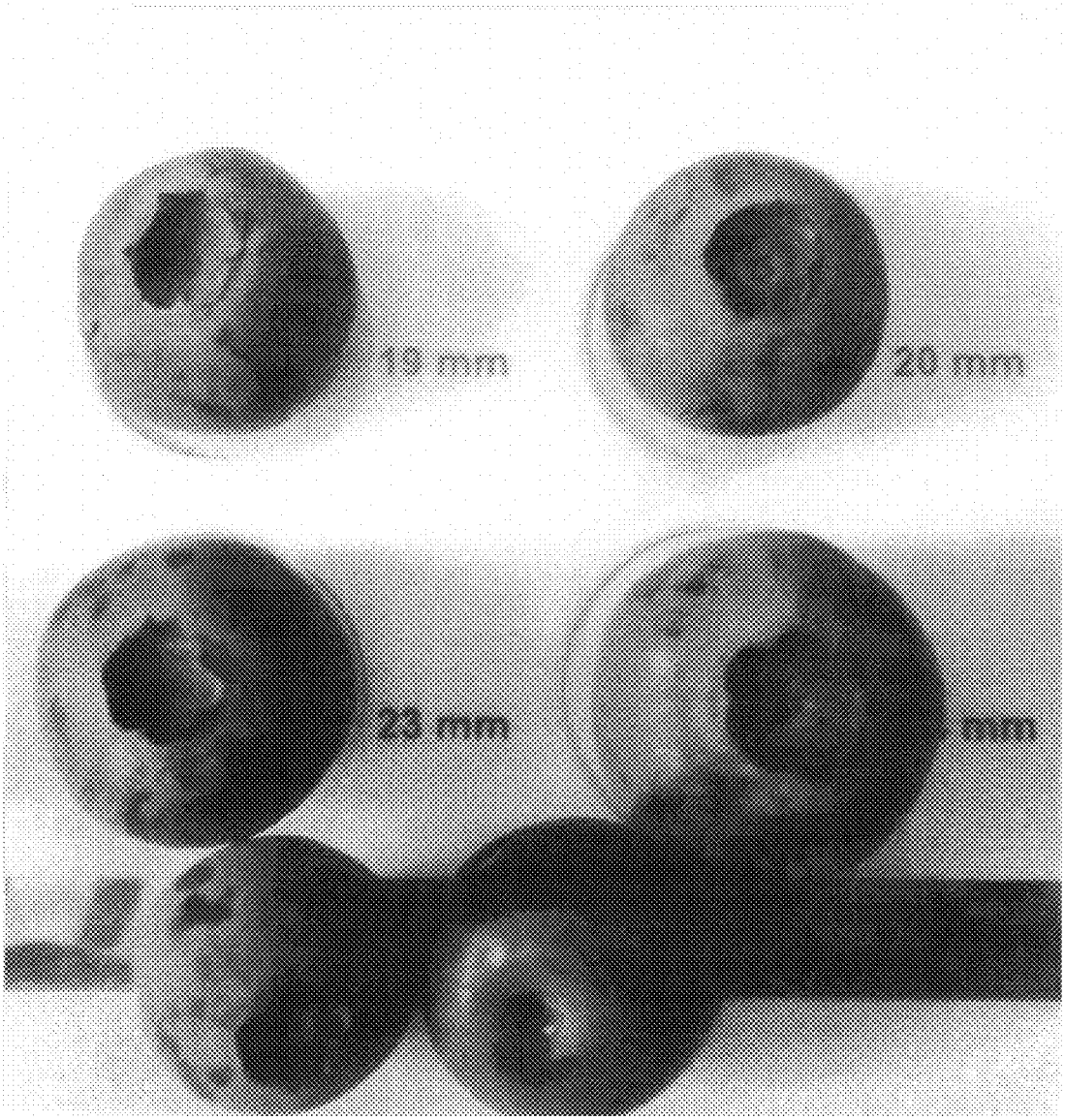
FIG. 5 shows a close view of typical mature dark blue berries of the new cultivar together with a basis for size comparison.

The chart used in the identification of the colors described herein is The R.H.S. Colour Chart of the Royal Horticultural Society, London, England. Ordinary color terms are to be accorded their customary dictionary significance. The description is based on the observation primarily during March-April 2008 of approximately five-year-old plants of the new cultivar which had been asexually reproduced by the rooting of cuttings while growing outdoors at Almonte, Huelva, Spain.

Plant:

*Growth habit.*—Generally upright.

*Height.*—Approximately 1.8 m at 5 years of age.

*Width.*—Approximately 3.5 m at 5 years of age.

*One-year canes.*—Commonly measure approximately 35.8 cm in length on average, approximately 6.8 mm in diameter on average at the base, approximately 4.8 mm in diameter on average near the tip, and commonly are near Yellow-Green Group 144B in coloration on a five-year-old plant.

*Five-year canes.*—Available five-year-old canes which had undergone some pruning have been found to measure approximately 73.4 cm in length on average, approximately 31.8 mm in diameter on average at the base, approximately 24 mm in diameter on average near the tip, and commonly are near Grey-Brown Group 199D in coloration.

*Foliage retention.*—Evergreen.

*Chill requirement.*—Less than 300 hours, and commonly on the order of 200 hours.

Foliage:

*Shape.*—Elliptic to elliptic-obovate.

*Length.*—Commonly approximately 64 mm on average.

*Width.*—Commonly approximately 32 mm on average.

*Apex.*—Acute.

*Base.*—Acute.

*Margin.*—Entire.

*Texture.*—Glabrous and non-glandular.

*Color.*—Green Group 137A on the upper (adaxial) surface, and Green Group 138B on the under (abaxial) surface.

Flowers:

*Time.*—Very early, at Almonte, Huelva, Spain, with first flower commonly at approximately November 7$^{th}$, and 50 percent bloom at approximately February 15$^{th}$.

*Number.*—Commonly approximately 5 flowers per bud on average.

*Color.*—When immature near Red-Purple Group 69A, and when mature White Group 155C.

*Length.*—Commonly approximately 11.5 mm on average.

*Corolla tube width.*—Commonly approximately 8.4 mm on average.

*Petals.*—5 in number and fused into a corolla tube.

*Petal size.*—Commonly approximately 9.3 mm in length on average, and approximately 4.2 mm in width on average.

*Pistil.*—Cone-shaped, approximately 0.8 to 1.5 mm in thickness at the base, the style length commonly is approximately 8.2 mm on average, and the coloration is light green.

*Stamen.*—Filaments possess pubescence and are light green in coloration, anthers are bronze in coloration, and some filaments are fused.

*Fertility.*—Self-fertile.

*Fragrance.*—Light.

Fruit:

*Time.*—Commonly from approximately February 25th to May 15$^{th}$ at Almonte, Huelva, Spain (i.e., approximately 10 weeks).

*Shape.*—Generally round and somewhat pumpkin-shaped (as illustrated).

*Height.*—Commonly approximately 16 mm on average.

*Width.*—Commonly approximately 20 mm on average.

*Weight.*—Approximately 2.45 g/berry on average during 2007 when plants were 4 years of age.

*Fruit scar.*—Approximately 2 mm in size.

*Fruit scar tear.*—Approximately 5 percent.

*Seed number.*—Commonly approximately 25 per berry on average.

*Seed size.*—Commonly approximately 1.4 mm in length and approximately 1 mm in width on average.

*Immature color.*—Commonly near Green Group 142C with bloom and Yellow-Green Group 145A without bloom.

*Mature color.*—Dark blue, Blue Group 103B with bloom and Black Group 202A without bloom.

*Productivity.*—Very abundant, approximately 4.52 Kg/plant on average during 2007 when plants were 4 years of age.

*Flavor.*—Displays a good acid flavor.

Development:

*Ability to store.*—The fruit stores well under refrigeration.

*Disease tolerance.*—No special sensitivity to common Blueberry diseases has been encountered during observations to date at Almonte, Huelva, Spain, and has shown more susceptible to common stem blight than the 'Sharpblue' cultivar (non-patented in the United States).

*Insects.*—Is susceptible to aphids and thrips.

*Cultural conditions.*—Does well in well drained soils and evergreen growing conditions in a low-chilling area.

Plants of the 'Romero' cultivar have not been observed under all possible environmental conditions to date, Accordingly, it is possible that the phenotypic expression may vary somewhat with changes in light intensity and duration, cultural practices, and other environmental conditions without variance in the genotype.

We claim:

1. A new and distinct Blueberry plant that possess the following combination of characteristics:

(a) flowers very early and forms fruit that ripens very early, (b) displays a strong and vigorous upright growth habit with attractive evergreen foliage, (c) is self-fertile, and is an excellent pollen producer, (d) displays a low chilling requirement, and (e) forms in abundance attractive dark blue berries that exhibit a pleasant acid flavor which commonly are amenable to harvest without stem retention;

substantially as herein shown and described.

* * * * *